United States Patent [19] … [11] 4,355,178
Töke et al. … [45] Oct. 19, 1982

[54] PROCESS FOR THE PREPARATION OF SUBSTITUTED ACYL UREAS

[75] Inventors: László Töke; István Bitter; Éva Kárpáti née Ádám; Tódor Pfliegel, all of Budapest, Hungary

[73] Assignee: Chinoin Gyogyszer es Vegyeszeti Termekek Gyara R.T., Budapest, Hungary

[21] Appl. No.: 198,050

[22] Filed: Oct. 17, 1980

[30] Foreign Application Priority Data

Oct. 19, 1979 [HU] Hungary ............................. CI-1977

[51] Int. Cl.$^3$ .......................................... C07C 127/22
[52] U.S. Cl. ....................................................... 564/44
[58] Field of Search ............................................ 564/44

[56] References Cited

U.S. PATENT DOCUMENTS

| | | | |
|---|---|---|---|
| 3,110,728 | 11/1963 | Takamatsu et al. | 564/44 X |
| 3,129,246 | 4/1964 | Harris et al. | 564/44 X |
| 3,301,896 | 1/1967 | Hayman et al. | 564/44 |
| 3,384,473 | 5/1968 | Pillon et al. | 564/44 X |
| 3,499,000 | 3/1970 | Langis | 564/44 X |
| 3,526,656 | 9/1970 | Butler | 564/44 X |
| 3,823,144 | 7/1974 | Schmitt et al. | 564/44 X |
| 4,150,160 | 4/1979 | Drabek et al. | 564/44 X |

FOREIGN PATENT DOCUMENTS 2005162  9/1970  Fed. Rep. of Germany ........ 564/44

Primary Examiner—Thomas A. Waltz
Attorney, Agent, or Firm—Karl F. Ross

[57] ABSTRACT

The invention relates to a process for the preparation of acyl ureas of formula (I)

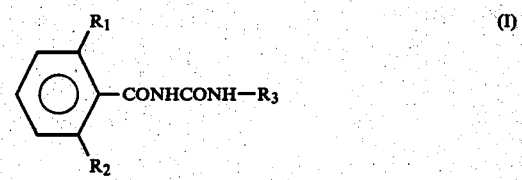

wherein
$R_1$ and $R_2$ are the same of different and each is halogen atom, preferably fluorine or chlorine atom, and
$R_3$ is a substituted aryl group.

The compounds of the invention can be prepared by reacting an urea of formula (II):

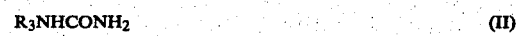

$R_3NHCONH_2$ (II)

wherein $R_3$ is as defined above, with an acid chloride of formula (III):

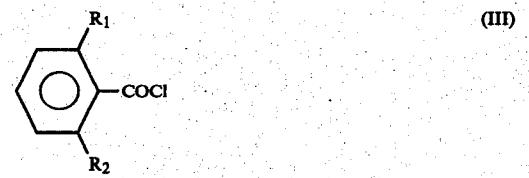

wherein $R_1$ and $R_2$ are as defined above, in an inert organic solvent at a temperature of from 20° C. to 100° C.

3 Claims, No Drawings

PROCESS FOR THE PREPARATION OF SUBSTITUTED ACYL UREAS

This invention relates to a process for the preparation of substituted acyl ureas having insecticidal activity.

Among the acyl ureas of formula (I)

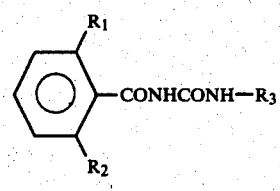

wherein:

$R_1$ and $R_2$ are the same or different and each is a halogen atom, and $R_3$ is a substituted aryl group, there are compounds which are very effective insecticides. These compounds are effective particularly in the case of larvae.

In the literature there are two processes for the preparation of compounds of formula (I) described. According to these processes aryl benzamides and aryl isocyanates or aroyl isocyanates and aryl amines are reacted so as to produce the acyl ureas [Ger. Off. No. 2 123 236 (1971), Neth. Appl. No. 705350 (1972), Wellinga, Kobus; Mulder, Rudolf; van Daalen, Jan J. (Res. Lab. Philips-Duphar B.V. Veesp. Neth.] and J. Agr. Food. Chem. 21, (3) 348-354 (1973).

As distinguished from the known methods, the starting materials of the invention can be produced simply and are cheap, the products can be obtained under mild reaction conditions and with good yields.

According to the invention the compounds of formula (I) are prepared by reacting a urea of formula (II):

$R_3NHCONH_2$          (II)

wherein $R_3$ is as defined above, with an acid chloride of formula (III):

wherein $R_1$ and $R_2$ are as defined above, in an inert organic solvent and, if desired the product is isolated.

The ureas of formula (II), wherein $R_3$ is as defined above, can be prepared from the suitable amines and urea by a known method [Tenney L. Davis and K. C. Blandhard, Org. Synth. Coll. 1, 442 (1932)].

The acylation can be carried out also with mixed anhydrides instead of the acid chlorides of formula (III). These mixed anhydrides can be produced by reacting a carboxylic acid with phosphorus oxychloride in the presence of a tertiary amine as an acid binding agent. These compounds can be applied without isolating.

The acylating reaction is carried out in an inert organic solvent at a temperature of from 20° C. to 100° C. with equimolecular amounts of the reagents or with a slight excess of the acid chloride either without use of an acid binding agent or in the presence of a tertiary amine. Preferred organic solvents are dioxane, benzene, ethyl acetate, acetonitrile and dichloromethane. Preferred tertiary amines are triethylamine and pyridine.

The following examples illustrate the preparation of the compounds of the invention.

EXAMPLE 1

17.04 g (0.1 mol) of N-(4-chlorophenyl)-urea are suspended in 100 ml of absolute dichloromethane then a solution of 17.6 g (0.1 mol) of 2,6-difluorobenzoylchloride in 100 ml of absolute dichloromethane is added dropwise. To this reaction mixture 14.5 ml (0,1 mol) of triethylamine are added.

The reaction mixture is stirred for 8 hours at the boiling point of the solvent. After cooling, the triethylamine hydrochloride is removed by washing with water. The precipitated product is filtered off, washed with aqueous alcohol and dried.

Yield: 22.2 g (71.5%).

Melting point: 216°-217° C.

Analysis: $C_{14}H_9ClF_2N_2O$ (310.45) calculated: C%: 54.11; H%: 2.89; N%: 9.01; found C%: 53.82; H%: 2.91; N%: 9.17.

EXAMPLE 2

To the suspension of 16.5 g (0.1 mol) of 95.5% 2,6-difluorobenzoic acid in 100 ml of absolute dichloromethane the mixture of 9.18 ml of phosphorus oxychloride in 100 ml of absolute dichloromethane is added under stirring at a temperature of from $-5°$ C. to 0° C.

The mixed anhydride of difluorobenzoic acid - phosphorus oxychloride is stirred for 1 hour at a temperature of 10° C. then 29 ml (0.2 mol) of triethylamine and 17.04 g (0.1 mol) of N-(4-chlorophenyl)-urea are added. The reaction mixture is stirred for 12 hours at the boiling point of the solvent. Then the reaction mixture is extracted with water, separated and the dichloromethane layer evaporated to dryness. The residue is smeared with aqueous methanol to give the product. The product is filtered off, washed with aqueous alcohol and dried.

Yield: 25.15 g (81%).

Melting point: a little protracting from 196° C. to 210° C.

The product is recrystallized from acetonitrile.

Analysis: calculated C%: 54.11; H%: 2.89; N%: 9.01; found: C%: 53.87; H%: 2.76; N%: 9.27.

| Example Nr. | Reagents | Reaction time (h) | Yield (%) | Melting point (°C.) | Analysis Calc. | Found |
|---|---|---|---|---|---|---|
| 3 | 17.04 g (0.1 mol) N—(4-chlorophenyl)-urea 17.6 g (0.1 mol) 2.6-difluorobenzoylchloride 100 ml abs. dioxan | 6 | 75 | 219 | C % 54.11 H % 2.89 N % 9.01 | C % 53.76 H % 2.97 N % 9.07 |
| 4 | 22.82 g (0,1 mol) N—(4-phenoxy- | | | | $C_{20}H_{14}F_2N_2O_3$ (368.34) | |

| Example Nr. | Reagents | Reaction time (h) | Yield (%) | Melting point (°C.) | Analysis Calc. | Analysis Found |
|---|---|---|---|---|---|---|
| | phenyl)-urea 17.6 g (0.1 mol) 2.6-difluoro-benzoylchloride 100 ml abs. dioxan 14.5 ml triethylamine | 10 | 78 | 203–205 | C % 65.15 H % 3.80 N % 7.60 | C % 64.87 H % 3.80 N % 7.26 |
| 5 | 17.04 g (0.1 mol) N—(4-chloro-phenyl)-urea 20.93 g (0.1 mol) 2,6-dichloro-benzoylchloride 150 ml abs. dichloroethane | 8 | 81 | 221 | $C_{14}H_9Cl_3N_2O_2$ (343.35) C % 48.90 H % 2.62 N % 8.15 | C % 49.26 H % 2.68 N % 8.50 |

We claim:

1. A process for the preparation of a compound of the formula:

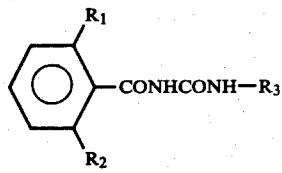

wherein $R_1$ and $R_2$ are the same or different and each is halogen; and $R_3$ is a substituted aryl group, which comprises the steps of acylating a compound of the formula (II):

$R_3NHCONH_2$ with a compound of the formula (III):

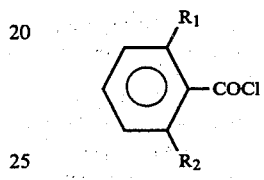

in an inert organic solvent at a temperature of from 20° C. to 100° C. and isolating the product.

2. The process defined in claim 1 wherein $R_1$ and $R_2$ are each fluoro or chloro.

3. The process defined in claim 1 wherein the inert organic solvent is dichloromethane.

* * * * *